(12) United States Patent
Fukuyama et al.

(10) Patent No.: US 7,041,975 B2
(45) Date of Patent: May 9, 2006

(54) SAMPLE ANALYZER

(75) Inventors: Hirofumi Fukuyama, Takasago (JP); Takahiro Yuki, Takasago (JP)

(73) Assignee: Kabushiki Kaisha Kobe Seiko Sho, Kobe (JP)

( * ) Notice: Subject to any disclaimer, the term of this patent is extended or adjusted under 35 U.S.C. 154(b) by 0 days.

(21) Appl. No.: 10/944,769

(22) Filed: Sep. 21, 2004

(65) Prior Publication Data

US 2005/0067567 A1    Mar. 31, 2005

(30) Foreign Application Priority Data

Sep. 26, 2003    (JP)    ............................. 2003-334638

(51) Int. Cl.
*H01J 32/282*    (2006.01)

(52) U.S. Cl. ....................... 250/309; 250/305

(58) Field of Classification Search ................ 250/309, 250/305, 287, 306, 307, 296, 297
See application file for complete search history.

(56) References Cited

U.S. PATENT DOCUMENTS

| | | | | |
|---|---|---|---|---|
| 4,829,179 | A | * | 5/1989 | Aoki et al. ................. 250/309 |
| 5,068,535 | A | * | 11/1991 | Rabalais ...................... 250/309 |
| 5,087,815 | A | * | 2/1992 | Schultz et al. .............. 250/309 |
| 5,350,920 | A | | 9/1994 | Fukuyama et al. |

FOREIGN PATENT DOCUMENTS

| | | | |
|---|---|---|---|
| JP | 2002-237271 | | 8/2002 |
| JP | 02004020459 A | * | 1/2004 |

OTHER PUBLICATIONS

"Kobe Steel Engineering Report" Research and Development Division, Kobe Steel Ltd., Sep. 2002; vol. 52; No. 2; pp. 53-56.

* cited by examiner

*Primary Examiner*—Kiet T. Nguyen
(74) *Attorney, Agent, or Firm*—Oblon, Spivak, McClelland Maier & Neustadt, P.C.

(57) ABSTRACT

A sample analyzer such as a Rutherford backscattering spectrometer for detecting ions that are elastically scattered by a sample is provided. A spectrum-measuring unit is shifted so that it can be positioned in accordance with a plurality of the scattering directions of the scattered ions in the sample analyzer. For example, the spectrum-measuring unit is shifted in an arc about the irradiation point of the ion beams along a guide rail. Alternatively, a vacuum container is composed of a fixed container holding the sample therein and a movable container hermetically and slidably connected to the fixed container and provided with detection ports. The movable container slides and thus the detection ports are shifted so that the detection ports can be positioned in accordance with the scattering directions. Accordingly, the detection ports, in turn, detection angles are easily changed, whereby a large sample can be analyzed.

16 Claims, 6 Drawing Sheets

SAMPLE ANALYZER

BACKGROUND OF THE INVENTION

1. Field of the Invention

The present invention relates to a sample analyzer for analyzing the composition of a sample by emitting accelerated light ions such as helium (He) or hydrogen (H) onto the sample to determine the energy spectrum of ions scattered resulting from elastic collisions with elements in the sample.

2. Description of the Related Art

Attention is being given to sample analyzers of a type that analyzes the composition of samples by measuring the energy spectrum of ions elastically scattered. Examples of such a sample analyzer include Rutherford backscattering spectrometry (RBS) which utilizes ions with high energy over 300 KeV.

The RBS can analyze the composition of a plurality of elements in a sample through measurement of the energy spectrum of scattered ions at various detection angles $\theta$.

A high resolution Rutherford backscattering spectrometer, described in "Kobe Steel Engineering Report" Research and Development Division, Kobe Steel Ltd., vol. 52, pp 53–56 can analyze the composition of samples with high depth resolution. More specifically, ions with single energy such as He or H are emitted onto a sample and the ions are elastically scattered by the elements in the sample. An electromagnetic spectrometer deflects the scattered ions having an energy spectrum in a magnetic field. The deflected energy spectrum is measured by a semiconductor ion detector.

Figure 6A:
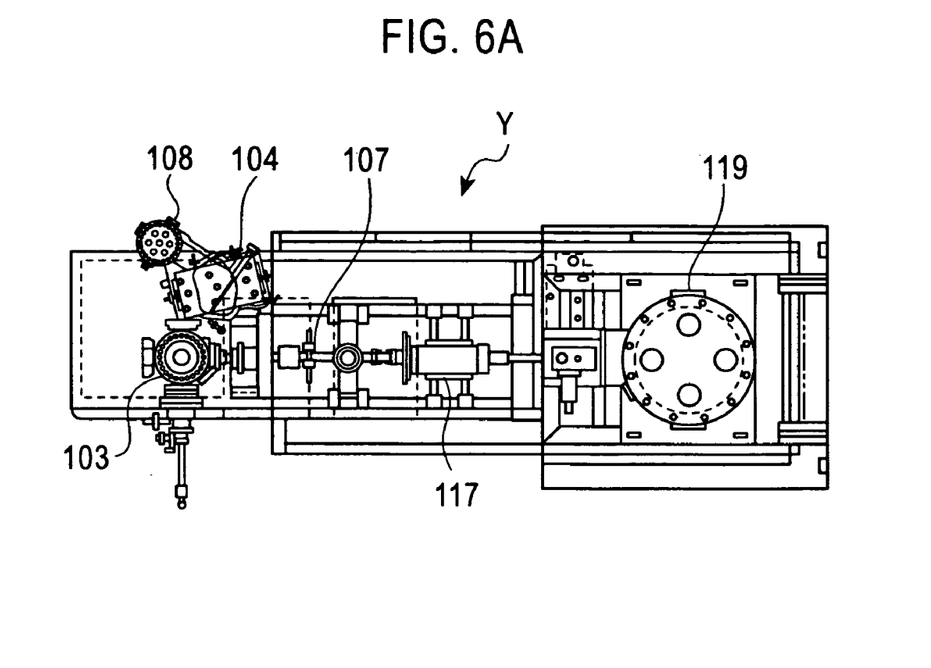
FIG. 6A is a top view of a Rutherford backscattering spectrometer Y of a known type.
Figure 6B:
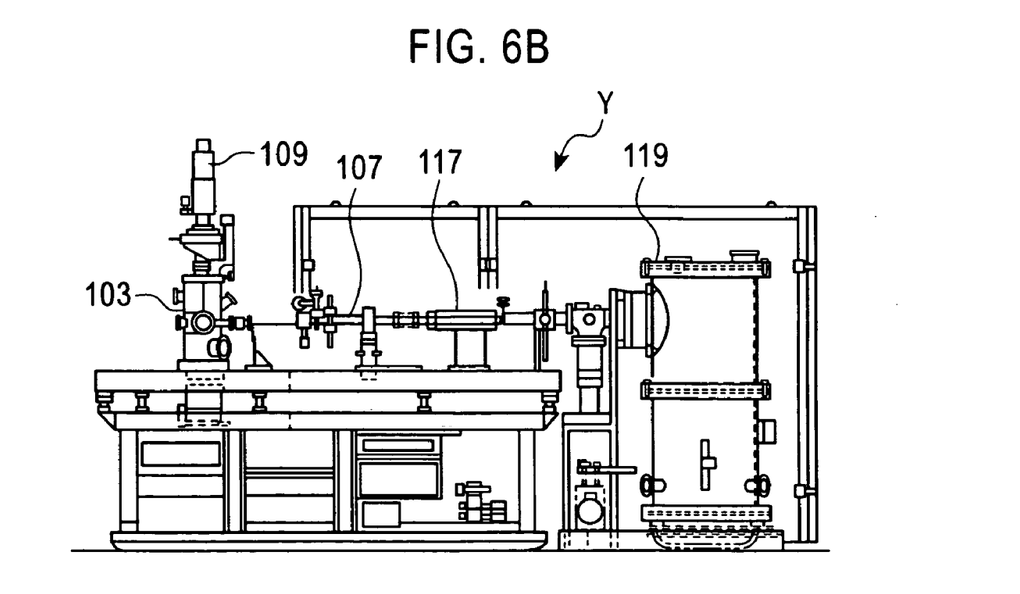
FIG. 6B is a side view of the Rutherford backscattering spectrometer Y.

The basic operation of a high resolution Rutherford backscattering spectrometer Y utilizing the aforementioned electromagnetic spectrometer will now be described in reference to FIGS. 6A and 6B. An ion source (not shown) in an accelerator 119 emits ion beams horizontally, and an E×B filter 117, where an electric field and a magnetic field are orthogonal to each other, selects monovalent helium ions out of the ion beams, for example. The E×B filter 117 deflects the trajectories of divalent helium ions, hydrogen atom ions, and hydrogen molecule ions, and a slit 107 eliminates these ions. The selected monovalent helium ions converge through a magnetic quadrupole lens (not shown) and are led into a chamber or vacuum container 103 to be emitted onto the surface of a sample 102 (not shown) from a horizontal direction, the sample 102 being supported by a goniometer 109. Then, the ion beams are elastically scattered by elements at the surface of and the inside of the sample. Part of the scattered ion beams enters an electromagnetic spectrometer 104 disposed in the vicinity of the chamber 103, and the trajectories of the ion beams are deflected through a magnetic field and are detected by an ion detector 108.

The electromagnetic spectrometer 104 includes a magnetic yoke, a pole piece, and an exciting coil, which are not shown in the drawing, and is rather large in size and weight. Since the exciting coil will heat up, the electromagnetic spectrometer 104 is normally disposed outside the chamber 103. The electromagnetic spectrometer 104 spectroscopically analyzes the ion beams elastically scattered by the elements of the sample in the chamber 103, and the ion beams having an energy spectrum are led into the ion detector 108. The energy distribution of the ion beams elastically scattered at the surface of the sample differs depending on the thin film structure of the sample such as elements on the surface or their composition, depth or position. Therefore, detection of the scattered ion beams by altering the detection angle $\theta$ (a scattering angle $\theta$ from the surface of the sample) can selectively analyze the thin film structure of the surface of the sample. Accordingly, in order to detect the ion beams at different detection angles $\theta$, a plurality of detection ports with different detection angles $\theta$ is disposed on the circumferential surface of the chamber 103 in the known high resolution Rutherford backscattering spectrometer. The electromagnetic spectrometer 104 can be connected to the plurality of detection ports.

Japanese Unexamined Patent Application Publication No. 2002-237271 discloses another type of sample analyzer. A magnetic pole is disposed inside a vacuum container, and an exciting coil is disposed outside the vacuum container. Magnetic yokes are also provided inside and outside the vacuum container and lead a magnetic flux generated by the exciting coil to the magnetic pole, which is isolated by the wall of the vacuum container from the exciting coil. Both an analysis of the magnetic field and detection of the energy spectrum of the scattered ions can be performed in the vacuum container where a sample is disposed. Accordingly, the analyzer can be miniaturized and an adverse effect of heating exciting coil on the analysis can be avoided.

Furthermore, an ion beam analyzing apparatus described in the U.S. Pat. No. 5,350,920 is also known as a sample analyzer utilizing ion beams.

According to the aforementioned high resolution Rutherford backscattering spectrometer, the electromagnetic spectrometer can be connected to a plurality of detection ports. However, the electromagnetic spectrometer needs to be attached to another detection port in order to change the detection angle of the scattered ions. Accordingly, the electromagnetic spectrometer has to be detached from a chamber or a bracket when attaching the electromagnetic spectrometer to another detection port. This is troublesome and also deteriorates the efficiency of the analysis.

Furthermore, when the electromagnetic spectrometer is detached from the chamber, the interior of the chamber is exposed to atmospheric air. Thus, after the electromagnetic spectrometer is attached to another detection port, the chamber has to be put back into a vacuum. Every time the electromagnetic spectrometer is attached to another detection port, the vacuum is broken in the chamber. Therefore, a long time is required in order to exhaust air in the chamber. Furthermore, when the sample is an ultra-thin film, exposure of the surface of the sample to air incurs contamination.

With all the aforementioned known analyzers, a plurality of beamline components such as a filter or a slit are disposed between the accelerator 119, which includes the ion source and an accelerating duct, and the chamber 103. To facilitate adjustment of the beamline components, the accelerator 119, the beamline components, and the chamber 103 are disposed in a line and ion beams are horizontally emitted from the accelerator 119 onto the sample. Alternatively, the directions of ion beams emitted vertically from the accelerator 119 are bent by, for example, a bending magnet so that the ion beams propagate horizontally. The sample is irradiated with the bent ion beams from a horizontal direction through the beamline components.

Although there has been a demand to analyze a large wafer in recent years, not a single known analyzer satisfies the demand. One of the reasons is that a wafer is inserted from a vertical direction with all the known analyzers and thus a large wafer cannot keep itself leveled when inserted. Another reason is that even if a wafer can be inserted while keeping itself leveled, a sample stage has to be rotated from a horizontal position to a substantially vertical position so that the ion beams are horizontally emitted on the wafer. However, keeping a large wafer in a substantially vertical position is unstable, resulting in breakage and contamination of the wafer. Furthermore, a chamber that can hold and rotate a large wafer is disadvantageously complicated. Accordingly, when a large wafer is a subject, it is preferred that a sample be placed laterally on a sample stage and ion beams be emitted vertically onto the sample.

SUMMARY OF THE INVENTION

The present invention is to solve the aforementioned problems and it is an object of the present invention to provide a sample analyzer in which detection ports are easily changed and alternation of the detection angles of ions that are emitted vertically or horizontally onto a sample and scattered by the sample is facilitated. Furthermore, according to the sample analyzer of the present invention, no breakage or contamination occurs even with a large sample.

According to a first aspect of the present invention, a sample analyzer includes: an ion generator for generating ion beams; an emitting mechanism for emitting the ion beams onto a sample; a vacuum container for holding the sample therein; at least one detection port for selectively leading scattered ions outside the vacuum container, the scattered ions being scattered by the sample in a plurality of scattering directions at predetermined scattering angles when the ion beams emitted from the emitting mechanism collide with the sample; a spectrum-measuring unit for measuring a spectrum of the scattered ions led through the detection port; and a measuring-unit-shifting member for shifting the spectrum-measuring unit such that the spectrum-measuring unit is positioned in accordance with the plurality of scattering directions of the scattered ions. The spectrum-measuring unit is easily detached from a detection port and attached to another detection port without completely disconnecting the spectrum-measuring unit including the electromagnetic spectrometer and the ion detector and thus the efficiency of changing detection ports is improved.

According to the first aspect of the present invention, preferably, a plurality of detection ports is disposed on the vacuum container, and the measuring-unit-shifting member is disposed in the vicinity of the vacuum container such that the spectrum-measuring unit is shifted in an arc about the irradiation point of the ion beams emitted onto the sample in the vacuum container, whereby the spectrum-measuring unit is positioned in accordance with the plurality of detection ports. Accordingly, the spectrum-measuring unit is easily connected to each of the detection ports disposed on the vacuum container having a column shape, for example.

According to the first aspect of the present invention, preferably, the sample analyzer includes a hermetically-connecting unit for hermetically connecting the spectrum-measuring unit to each of the detection ports, the spectrum-measuring unit being positioned in accordance with each detection port.

According to the first aspect of the present invention, preferably, the measuring-unit-shifting member is an arched rail disposed in the vicinity of the vacuum container, and the spectrum-measuring unit is shifted along the rail.

According to the first aspect of the present invention, preferably, the sample analyzer includes a detection-port-shifting unit for shifting the detection port disposed on the vacuum container such that the detection port is positioned in accordance with the plurality of scattering directions of the scattered ions. The vacuum container may be composed of a fixed container holding the sample therein and a movable container hermetically and slidably connected to the fixed container and provided with the detection port, and the detection-port-shifting unit enables the movable container to slide so that the detection port is shifted. When the spectrum-measuring unit is attached to another detection port, the vacuum is maintained in the vacuum container. Therefore, the detection angle of the scattered ions is easily altered by changing the detection port to which the spectrum-measuring unit is attached while a vacuum is maintained in the vacuum container. In addition, the detection angle of the scattered ions can be flexibly determined. Furthermore, since a vacuum is maintained in the vacuum container, breakage and contamination of the sample is avoided.

According to the first aspect of the present invention, preferably, the emitting mechanism emits the ion beams onto the sample in a vertical direction. Furthermore, the sample analyzer includes a bending unit for bending the ion beams emitted from the ion generator in a horizontal direction so that the ion beams propagate in a vertical direction, and the emitting mechanism emits the ion beams onto the sample in the vertical direction through the bending unit. Even when a large wafer is a subject, it is unnecessary to hold the large wafer in an unstable vertical position. Accordingly, the wafer will not break and thus the composition analysis of the wafer is advantageously conducted.

According to the first aspect of the present invention, preferably, the sample analyzer includes a sample-supplying unit for supplying the sample in a horizontal direction into the vacuum container. Accordingly, the sample can be stably inserted into the container while keeping itself leveled. Therefore, no breakage occurs even with a large sample.

According to the first aspect of the present invention, preferably, the sample analyzer includes a sample-holding unit for rotatably holding the sample, the sample-holding unit being disposed opposite from the spectrum-measuring unit with respect to the irradiation point of the ion beams emitted onto the sample in the vacuum container.

According to a second aspect of the present invention, a sample analyzer includes: an ion generator for generating ion beams; an emitting mechanism for emitting the ion beams onto a sample; a vacuum container for holding the sample therein; at least one detection port for selectively leading scattered ions outside the vacuum container, the scattered ions being scattered by the sample in a plurality of scattering directions at predetermined scattering angles when the ion beams emitted from the emitting mechanism collide with the sample; and a spectrum-measuring unit for measuring a spectrum of the scattered ions led through the detection port. In the sample analyzer, the emitting mechanism emits the ion beams onto the sample in a vertical direction.

Thus, even when a large wafer is a subject, it is unnecessary to hold the large wafer in an unstable vertical position. Accordingly, the wafer will not break and thus the composition analysis of the wafer is advantageously conducted.

According to the first and second aspects of the present invention, preferably the sample analyzer is a Rutherford backscattering spectrometer.

As described above, according to the present invention, the sample analyzer such as a Rutherford backscattering spectrometer for detecting scattered ions that are emitted horizontally or vertically onto a sample and scattered by the sample is provided with the spectrum-measuring unit. The spectrum-measuring unit is shifted so that it is positioned in accordance with the plurality of scattering directions of the scattered ions. More specifically, the spectrum-measuring unit is shifted in an arc about the irradiation point of the ions along the arched rail. Accordingly, detection ports can be easily changed without completely disconnecting the spectrum-measuring unit including the electromagnetic spectrometer and the ion detector and thus the detection ports are effectively changed.

Furthermore, the detection ports disposed on the vacuum container are shifted so that they are positioned in accordance with the plurality of scattering directions of the scattered ions. More specifically, the vacuum container is composed of the fixed container holding the sample therein and the movable container that is provided with the detection ports and is hermetically and slidably connected to the fixed container. Even in a case where the detection ports are shifted by sliding the movable container so that the detection port to which the spectrum-measuring unit is attached is changed, a vacuum is maintained in the vacuum container. Therefore, the detection ports are shifted while a vacuum is maintained in the vacuum container and the detection angles of the scattered ions are easily altered. Furthermore, breakage and contamination of the sample can be avoided.

DESCRIPTION OF THE PREFERRED EMBODIMENTS

Embodiments of the present invention will now be described in reference to the accompanying drawings. It should be noted that the following embodiments are merely examples and not to limit the scope of the present invention.

Figure 1:
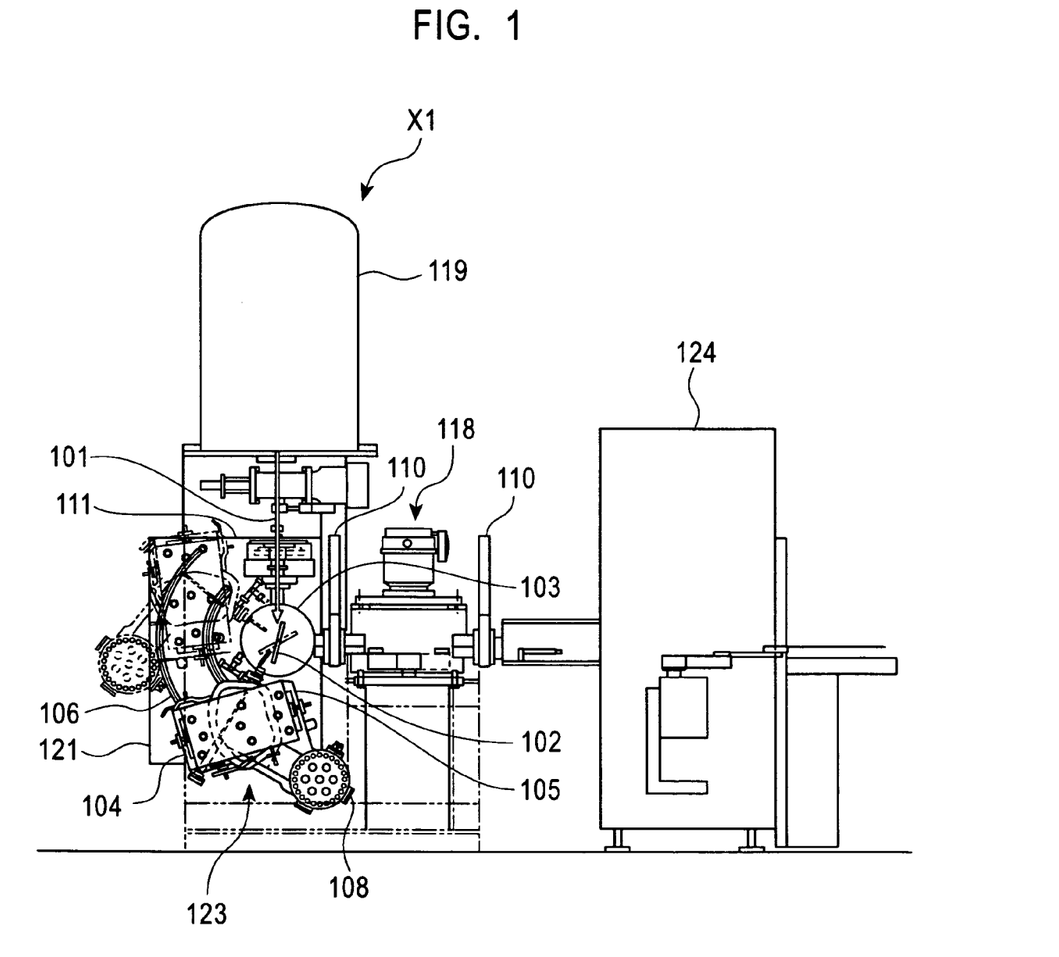
FIG. 1 is a side view of a Rutherford backscattering spectrometer X1 according to a first embodiment of the present invention.
Figure 2:
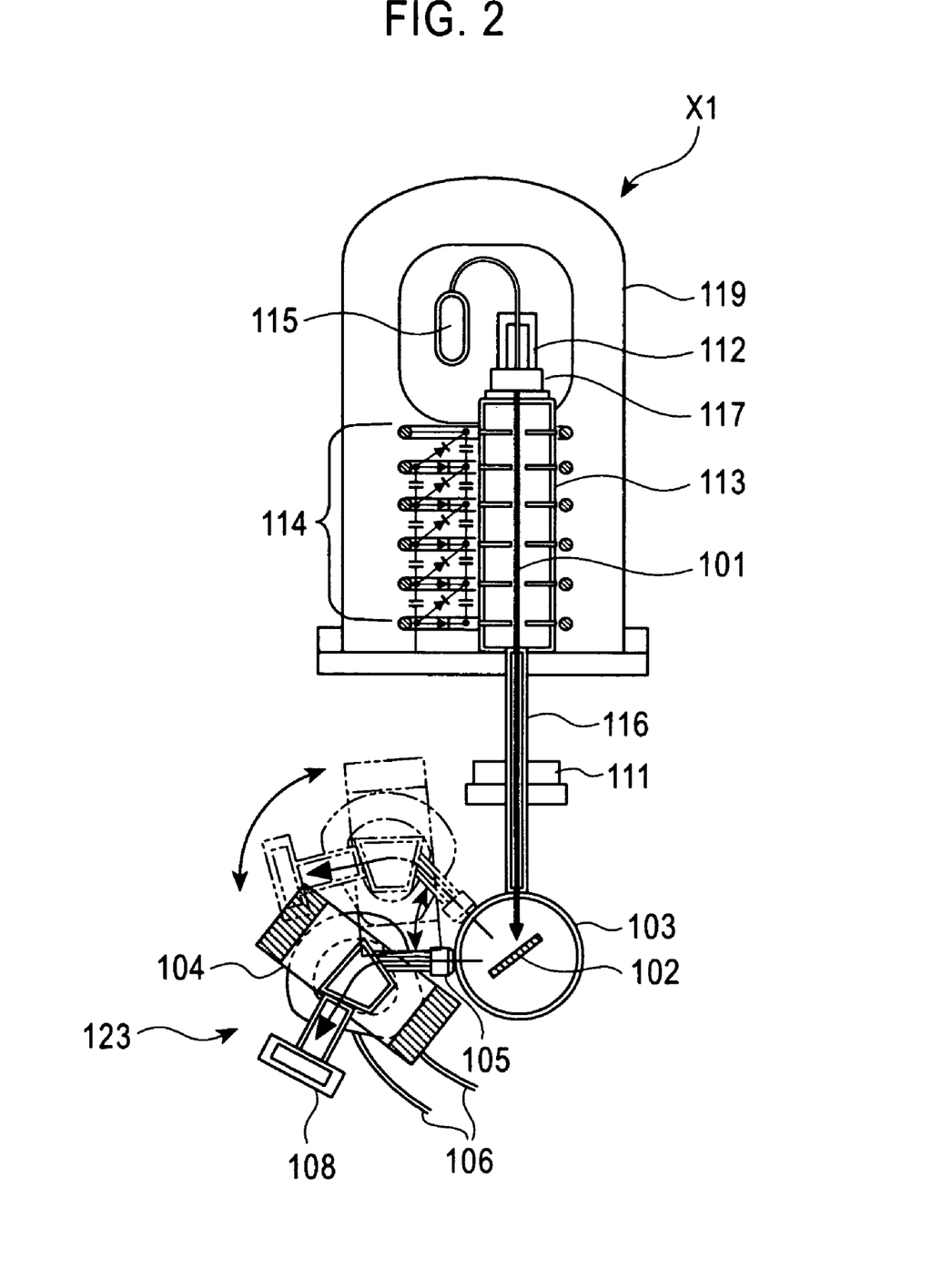
FIG. 2 is a schematic cross-sectional view of the Rutherford backscattering spectrometer X1 according to the first embodiment of the present invention.

Referring to FIGS. 1 and 2, a Rutherford backscattering spectrometer X1 according to a first embodiment of the present invention will now be described. The Rutherford backscattering spectrometer X1 is an example of a sample analyzer for analyzing the composition of a sample by measuring the energy spectrum of ions elastically scattered.

In the Rutherford backscattering spectrometer X1, an accelerator or ion generator 119 is disposed vertically above a chamber or vacuum container 103. In this accelerator 119, helium from a helium bottle 115 is ionized through an ion source 112, and monovalent helium ions or ion beams 101 selectively pass through an E×B filter 117 and are sent to an accelerating duct 113. A high voltage circuit 114 supplies high voltage to the accelerating duct 113, and the helium ions 101 with high energy are accelerated. The accelerated ions 101 are emitted vertically downward and pass through a beam duct 116. A Q magnet 111 is disposed in the midway of the beam duct 116, and ions 101 converge by the Q magnet 111. A sample 102 in the chamber 103 is irradiated with the ions 101. The structure in which ions from the accelerator 119 are emitted onto the sample 102 is defined by an emitting mechanism.

Ions collide with the sample 102 and are elastically scattered at the surface or the interior of the sample 102. Scattered ions entering a detection port 105 connected to a spectrum-measuring unit 123 are selectively analyzed spectroscopically by the electromagnetic spectrometer 104, and a selected energy spectrum is detected by the ion detector 108 constituting the spectrum-measuring unit 123.

The chamber 103 is a column and a turbomolecular pump 130 is disposed in the vicinity of the chamber 103. The turbomolecular pump 130 exhausts air in the chamber 103 so that a vacuum is maintained in the chamber 103. The chamber 103 is provided with detection ports 105. The ions are emitted onto the sample 102 and are scattered by the sample 102. The detection ports 105 selectively lead the scattered ions outside the chamber 103, the scattered ions being scattered in a plurality of directions at predetermined scattering angles. The detection port 105 is hermetically connected to the electromagnetic spectrometer 104 in order to detect the ions scattered in a plurality of directions at a plurality of angles. A sample stage (not shown) for holding the sample 102 is disposed at the center axis (column axis) of the chamber 103. Among the ions elastically scattered by the sample 102, the ions entering the detection port 105 connected to the electromagnetic spectrometer 104 are led into the electromagnetic spectrometer 104. The sample stage is supported so as to rotate in the circumferential direction of the chamber 103 about the center axis of the chamber 103. A goniometer or sample-holding unit 109 is disposed outside the chamber 103 on one of the planes orthogonal to the circumferential surface of the chamber 103 and is drivingly connected to the sample stage. The goniometer 109 holds the sample stage and rotates the sample stage in the circumferential direction of the chamber 103. To avoid interference with the electromagnetic spectrometer 104, the goniometer 109 is rotatably disposed opposite from the spectrum-measuring unit 123 with respect to the irradiation point of the ion beams 101 emitted onto the sample 102 in the chamber 103.

A vacuum handling-robot or sample-supplying unit 118 places the sample 102 onto the sample stage. The vacuum handling-robot 118 supplies the leveled sample 102 onto the sample stage in the chamber 103 from a horizontal direction. Therefore, an inlet for the sample 102 is disposed on the circumferential surface of the chamber 103. An atmospheric handling-robot 124 supplies the sample 102 to the vacuum handling-robot 118.

As described above, the energy spectrum of the scattered ions is measured by altering the detection angle θ, whereby the elements of the sample are analyzed. When analyzing the composition of the sample, it is necessary to change the detection port 105 to which the electromagnetic spectrometer 104 is attached. Unlike Rutherford backscattering spectrometer of a known type, according to the Rutherford backscattering spectrometer X1 of the present invention, the spectrum-measuring unit 123 is easily detached from a detection port 105 and attached to another detection port 105 without completely disconnecting the spectrum-measuring unit 123 including the electromagnetic spectrometer 104 and the ion detector 108. A guide rail or measuring-unit-shifting member 106 is disposed on a guide rail platform 121. The guide rail 106 shifts the electromagnetic spectrometer 104 so that the electromagnetic spectrometer 104 can be positioned in accordance with the scattering directions of the scattered ions. More specifically, in order to shift the spectrum-measuring unit 123 to the positions corresponding to a plurality of detection ports 105, the guide rail 106 is disposed in the vicinity of the chamber 103 so that the spectrum-measuring unit 123 moves in an arc about the irradiation point of the ion beams 101, which are emitted onto the sample held in the chamber 103. The guide rail 106 is arched on the guide rail platform 121 in the vicinity of the chamber 103. The spectrum-measuring unit 123 can be shifted to another detection port 105 along the guide rail 106. Therefore, changing the detection ports 105 is readily accomplished without completely disconnecting the spectrum-measuring unit 123. In this case, the spectrum-measuring unit 123 is required to include a sliding mechanism connected to the guide rail 106. The sliding mechanism enables the spectrum-measuring unit 123 to slide along the guide rail 106. To maintain the chamber 103 vacuum, a seal or hermetically-connecting unit such as an 0-ring or labyrinth seal is provided at the portion connecting the detection port 105 and the spectrum-measuring unit 123. Thus, the spectrum-measuring unit 123 is hermetically connected to the detection port 105, the spectrum-measuring unit 123 being positioned in accordance with the detection port 105.

The spectrum-measuring unit 123 can be manually or electrically moved along the guide rail 106. When the spectrum-measuring unit 123 is electrically moved, a driving unit such as a motor is used. For example, a driving signal corresponding to a predetermined number of rotations is output to the motor in response to a positional signal of the spectrum-measuring unit 123 detected by a position-detecting unit, which can detect the position of the spectrum-measuring unit 123 such as a potentiometer or a rotary encoder. The spectrum-measuring unit 123 is shifted by remote manipulation and thus is desirably positioned.

Figure 3A:
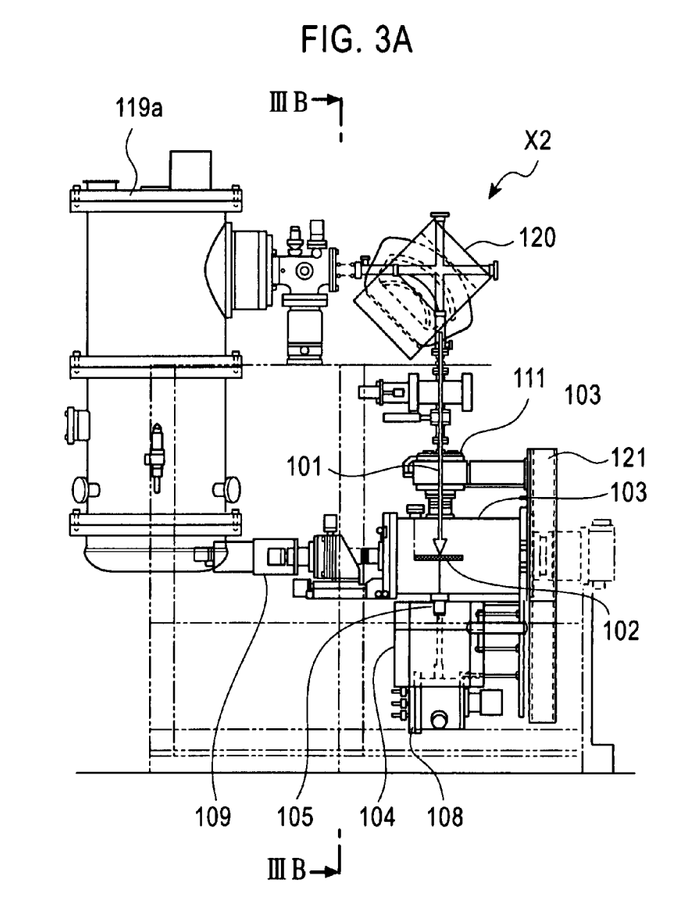
FIG. 3A is a side view of a Rutherford backscattering spectrometer X2 according to a second embodiment of the present invention.
Figure 3B:
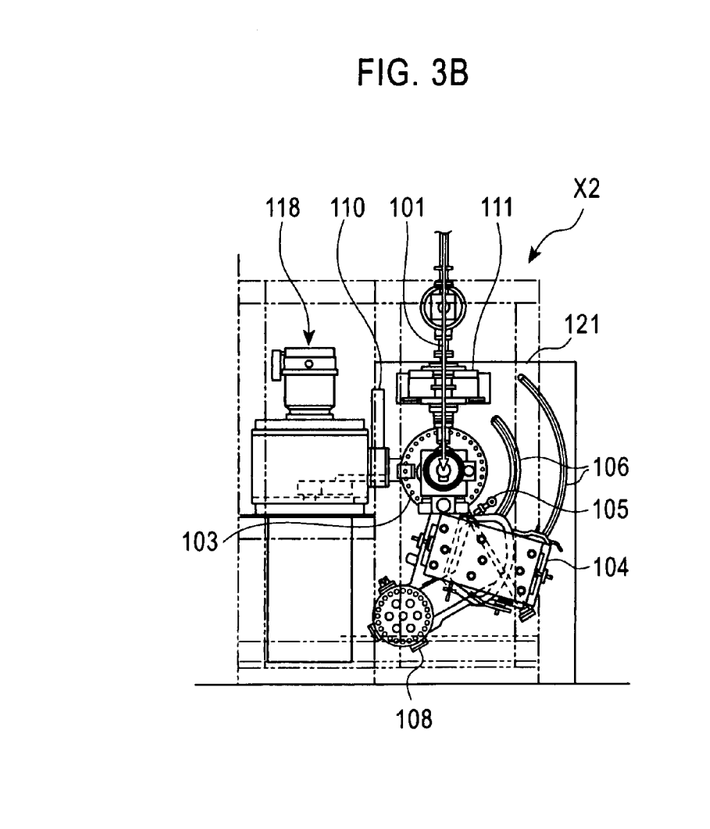
FIG. 3B is a cross-sectional view taken along line IIIB—IIIB in FIG. 3A.

Referring to FIGS. 3A and 3B, a Rutherford backscattering spectrometer X2 according to a second embodiment of the present invention will now be described. In the Rutherford backscattering spectrometer X1 of the first embodiment, the ion beams 101 are emitted vertically downward from the accelerator 119, and the sample 102 placed in the chamber 103 is irradiated with the ion beams 101 from the vertical direction. By contrast, according to the Rutherford backscattering spectrometer X2 of the second embodiment, the ion beams 101 are horizontally emitted from an accelerator 119a, and a bending magnet or bending unit 120 bends the ion beams 101 so that the ion beams 101 travel vertically downward. Similar to the first embodiment, the deflected ion beams 101 are emitted onto the sample 102 from the vertical direction.

As described above, according to the Rutherford backscattering spectrometer X2, the ion beams 101 emitted horizontally from the accelerator 119a are bent by the bending magnet 120 so that the sample 102 is irradiated with the ion beams 101 from the vertical direction. Thus, the guide rail 106 can also be applied to the Rutherford backscattering spectrometer X2, and the guide rail 106 enables the spectrum-measuring unit 123 to be shifted so that the spectrum-measuring unit 123 is positioned in accordance with the scattering directions of the scattered ions.

Figure 4:
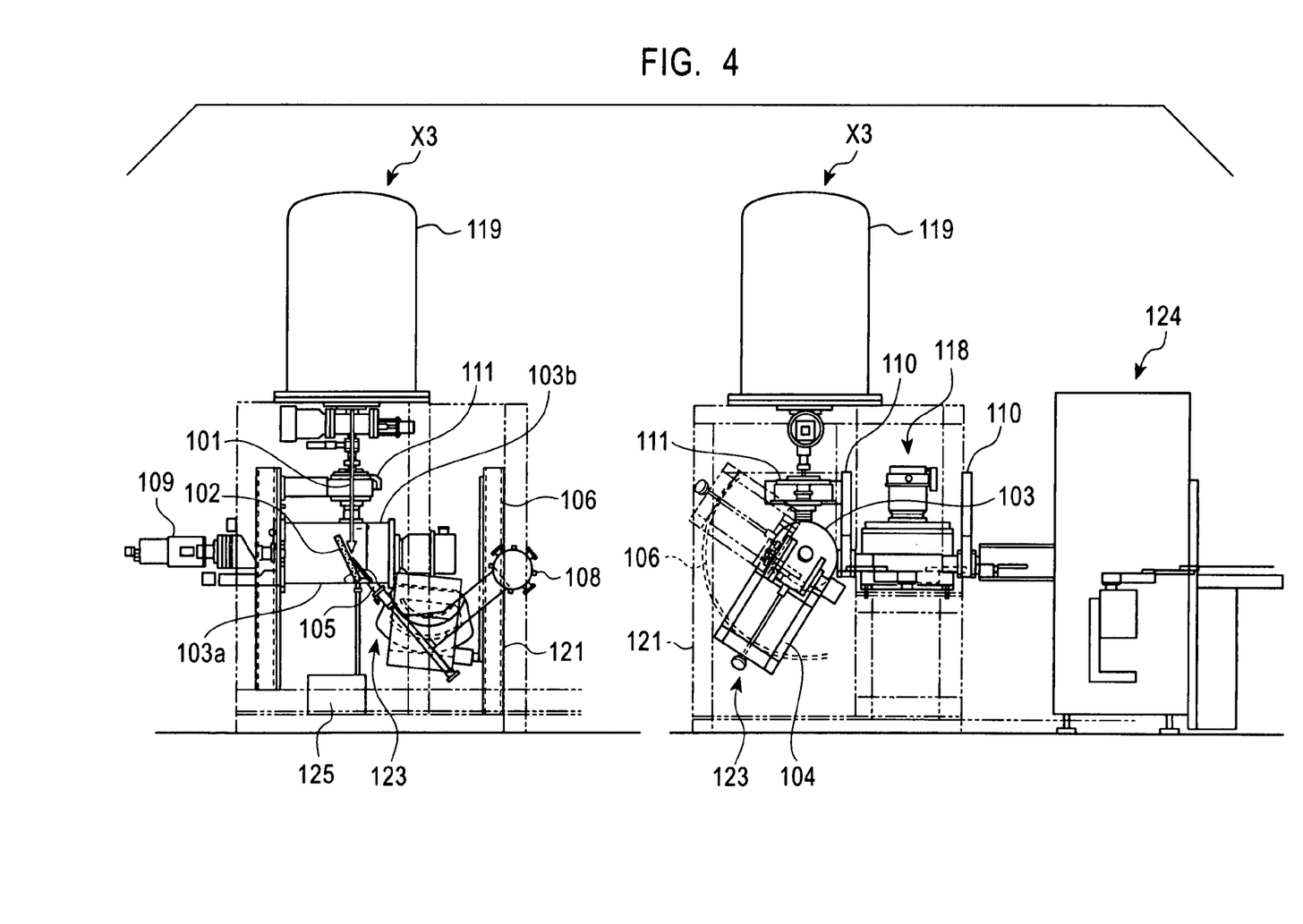
FIG. 4 is a side view of a Rutherford backscattering spectrometer X3 according to a third embodiment of the present invention.
Figure 5A:
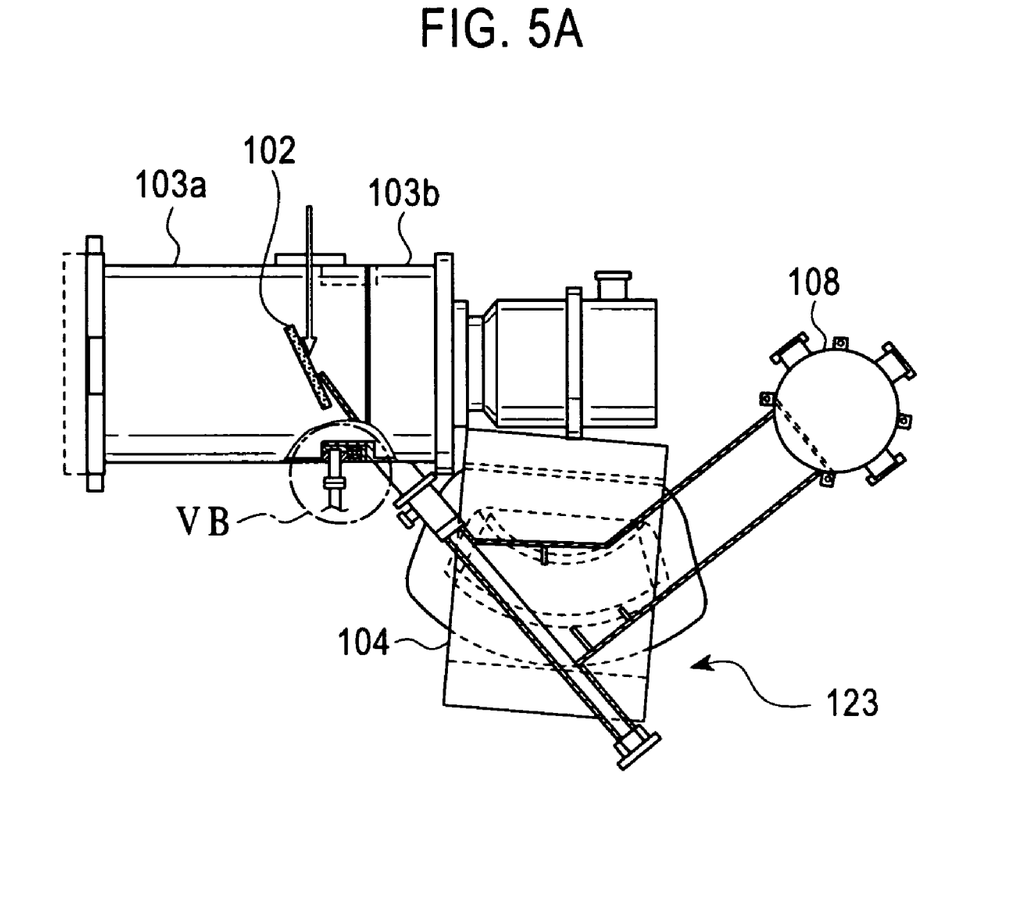
FIG. 5A is an enlarged view of a vacuum container and its vicinities in the Rutherford backscattering spectrometer X3 shown in FIG. 4.
Figure 5B:
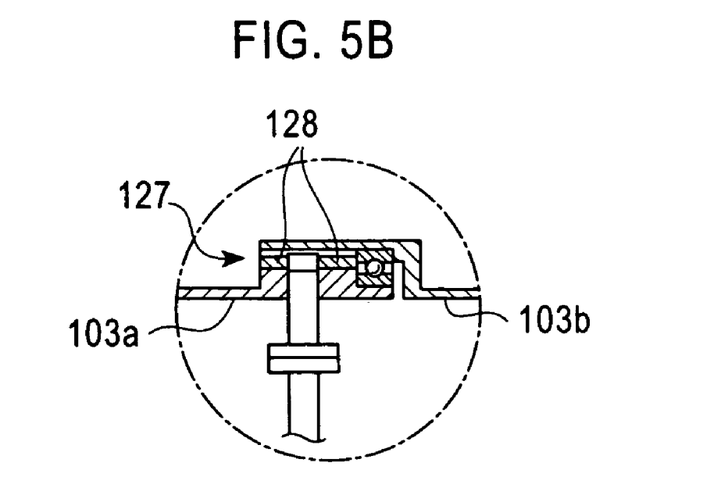
FIG. 5B is a detailed view of a connecting portion and its vicinities shown in FIG. 5A.

Referring to FIGS. 4, 5A, and 5B, a Rutherford backscattering spectrometer X3 according to a third embodiment will now be described.

A differential pump 125 is provided in the Rutherford backscattering spectrometer X3. A detection-port-shifting unit is also provided in the Rutherford backscattering spectrometer X3. The detection-port-shifting unit shifts the detection ports 105 disposed on the chamber 103 so that the detection ports 105 are positioned in accordance with the scattering directions of the ions scattered by the sample 102. More specifically, a chamber 103 is composed of a fixed container 103a holding the sample 102 therein and a movable container 103b, which is hermetically and slidably connected to the fixed container 103a. The detection ports 105 are provided on the movable container 103b. The movable container 103b slides in the circumferential direction of the chamber 103 so that the detection ports 105 disposed on the movable container 103b are shifted. According to the Rutherford backscattering spectrometer X3, when attaching the spectrum-measuring unit 123 to another detection port, a vacuum is maintained in the chamber 103. Thus, the detection angles of the scattered ions are easily altered and breakage and contamination of the sample 102 can be avoided.

Since it is necessary that a vacuum be maintained in the chamber 103, a connecting portion 127 between the fixed container 103a and the movable container 103b needs to be well sealed so that fluid such as air will not enter through the connecting portion 127. Therefore, a seal 128 such as a labyrinth seal is provided at the connecting portion 127. The seal 128 is not only high quality but also allows the movable container 103b to slide along the fixed container 103a. The seal 128 connects the fixed container 103a to the movable container 103b so that a vacuum is maintained in the chamber 103. The chamber 103 is required to be in ultrahigh vacuum. Thus, as shown in FIG. 5B, the differential pump 125 is connected to the gaps between a plurality of seals 128 disposed in the connecting portion 127 so that fluid such as air from outside is exhausted to keep the chamber 103 in ultrahigh vacuum.

Alternatively, instead of the seal 128, a plurality of labyrinths may be provided on one of the surfaces where the movable container 103b slides along the fixed container 103a. Accordingly, the connecting portion 127 is hermetically sealed by labyrinth effect.

Similar to the Rutherford backscattering spectrometer X1 of the first embodiment, the spectrum-measuring unit 123 may be shifted along the guide rail 106 by a driving unit such as a motor. In this case, the driving unit has to be operatively associated with the movable container 103b to drive the spectrum-measuring unit 123.

What is claimed is:

1. A sample analyzer comprising:
   an ion generator for generating ion beams;
   an emitting mechanism for emitting the ion beams onto a sample;
   a vacuum container for holding the sample therein;
   at least one detection port for selectively leading scattered ions outside said vacuum container, the scattered ions being scattered by the sample in a plurality of scattering directions at predetermined scattering angles when the ion beams emitted from said emitting mechanism collide with the sample;
   a spectrum-measuring unit for measuring a spectrum of the scattered ions led through said detection port; and
   a measuring-unit-shifting member for shifting the spectrum-measuring unit such that said spectrum-measuring unit is positioned in accordance with the plurality of scattering directions of the scattered ions.

2. The sample analyzer according to claim 1, wherein said at least one detection port comprises a plurality of detection ports disposed on said vacuum container, and said measuring-unit-shifting member is disposed in the vicinity of said vacuum container such that the spectrum-measuring unit is shifted in an arc about the irradiation point of the ion beams emitted onto the sample in said vacuum container, whereby said spectrum-measuring unit is positioned in accordance with the plurality of detection ports.

3. The sample analyzer according to claim 2, further comprising a hermetically-connecting unit for hermetically connecting said spectrum-measuring unit to each of said detection ports, said spectrum-measuring unit being positioned in accordance with each detection port.

4. The sample analyzer according to claim 1, wherein said measuring-unit-shifting member is an arched rail disposed in the vicinity of said vacuum container, and said spectrum-measuring unit is shifted along the rail.

5. The sample analyzer according to claim 1, further comprising a detection-port-shifting unit for shifting the detection port disposed on said vacuum container such that said detection port is positioned in accordance with the plurality of scattering directions of the scattered ions.

6. The sample analyzer according to claim 5, wherein said vacuum container is composed of a fixed container holding the sample therein and a movable container hermetically and slidably connected to said fixed container and provided with said detection port, and said detection-port-shifting unit enables said movable container to slide so that said detection port is shifted.

7. The sample analyzer according to claim 1, wherein said emitting mechanism emits the ion beams onto the sample in a vertical direction.

8. The sample analyzer according to claim 1, further comprising a bending unit for bending the ion beams emitted from said ion generator in a horizontal direction so that the ion beams propagate in a vertical direction, and said emitting mechanism emits the ion beams onto the sample in the vertical direction through said bending unit.

9. The sample analyzer according to claim 1, further comprising a sample-supplying unit for supplying the sample in a horizontal direction into said vacuum container.

10. The sample analyzer according to claim 1, further comprising a sample-holding unit for rotatably holding the sample, said sample-holding unit being disposed opposite from said spectrum-measuring unit with respect to the irradiation point of the ion beams emitted onto the sample in said vacuum container.

11. The sample analyzer according to claim 1, wherein said sample analyzer is a Rutherford backscattering spectrometer.

12. A sample analyzer comprising:
an ion generator for generating ion beams;
an emitting mechanism for emitting the ion beams onto a sample;
a vacuum container for holding the sample therein;
at least one detection port for selectively leading scattered ions outside said vacuum container, the scattered ions being scattered by the sample in a plurality of scattering directions at predetermined scattering angles when the ion beams emitted from said emitting mechanism collide with the sample; and
a spectrum-measuring unit for measuring a spectrum of the scattered ions led through said detection port, wherein said emitting mechanism emits the ion beams onto the sample in a vertical direction with respect to a gravitational field affecting the sample analyzer.

13. The sample analyzer according to claim 12, further comprising a bending unit for bending the ion beams emitted from said ion generator in a horizontal direction so that the ion beams propagate in a vertical direction, and said emitting mechanism emits the ion beams onto the sample in the vertical direction through the bending unit.

14. The sample analyzer according to claim 12, further comprising a sample-supplying unit for supplying the sample in a horizontal direction into said vacuum container.

15. The sample analyzer according to claim 12, further comprising a sample-holding unit for rotatably holding the sample, said sample-holding unit being disposed opposite from said spectrum-measuring unit with respect to the irradiation point of the ion beams emitted onto the sample in said vacuum container.

16. The sample analyzer according to claim 12, wherein said sample analyzer is a Rutherford backscattering spectrometer.

* * * * *